June 20, 1972 C. F. PENNOCK Plant Pat. 3,219
DRACAENA CELES
Filed Dec. 10, 1970
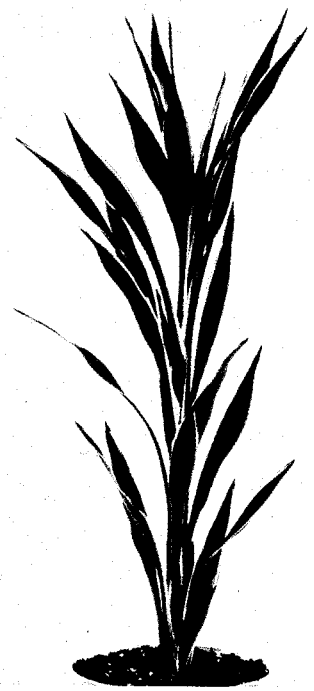
INVENTOR
CHARLES F. PENNOCK
J. Gibson Semmes
ATTORNEY

United States Patent Office

Plant Pat. 3,219
Patented June 20, 1972

3,219

*DRACAENA CELES*

Charles Frederick Pennock, San Juan, Puerto Rico, assignor to Cerro Gordo Nursery, Inc., Durado, Puerto Rico

Filed Dec. 16, 1970, Ser. No. 98,969
Int. Cl. A01h *5/00*
U.S. Cl. Plt.—88 1 Claim

A new and distinct variety of ornamental plant of the genus Dracaena, originated as a mutation of the variety *Dracaena sanderiana* (unpatented).

The mutation was discovered in the nursery located in the municipality of Bayamon, Ward of Toa Baja.

It has been asexually reproduced at the same location, by means of cuttings and its distinguishing features appear to be permanent.

The invention is related to the Dracaena plant identified in United States Plant Patent 1,627, dated Aug. 6, 1957, inventor applicant hereunder, Charles F. Pennock.

The accompanying illustration depicts a color photograph of a potted plant of the new variety in approximately its true colors, the plant shown being approximately sixty-five (65) weeks old at the time of photographing. The specimen was at that time approximately twelve (12) inches tall from the ground to the tip of the central leaf. In the following detailed description of my new variety, the color method chose for identification has been taken of the Inter-Society Color Council—National Bureau of Standards, Supplement to Circular 553, the ISCC Method of designating color and a dictionary of color names.

The new variety is a herbaceus plant and has a small narrow lanceloate leaf 4 to 10 inches in length, including the prominent petiole which tapers gradually from the blade and is ¼″ to 1″ in width. As in the mother plant *Drac. sanderiana,* the leaves are compactly grouped, but erect rather than pendant. The texture is also much harder or stiffer than the parent.

The plant grows straight and erect with its leaves regularly spaced along the full length of the cane. The habit of growth is somewhat slower than the parent, growing about 8″ the first year, if allowed to grow without cutting. Because of the pleasing color pattern, this new variety makes an excellent house plant. It propagates true from cuttings, rooting easily at each node which is placed below the earth surface.

The upper surface of the leaves corresponds to Color No. 151 Dark Green. The color of the opposite side or underside of the leaves corresponds to Color No. 150 Gray Green. The outstanding features include the novel striping of the leaves, represented by a single, narrow whitish marginal stripe 1/16″ wide.

*Comparisons*

The variety most like my new variety is the Dracaena plant illustrated and described in Plant Patent No. 1,627 aforesaid. The principal difference between the varieties lie in the color patterns of their leaves as follows:

(1) The color pattern of the leaves of my new variety consist of: a dark green surface with gray green bottom.

(2) The leaves of the mutant hereof are somewhat narrower and have a more upright tendency than the parent *Dracaena sanderiana,* unpatented.

(3) There is a greater proportion of green and silvery tones with white edges than is found in the parent.

Having thus disclosed my discovery, I claim:

1. The new and distinct variety of Dracaena plant substantially as herein shown and described, characterized particularly by small narrow lanceloate leaves, including the prominent petiole, the leaves being compactly grouped and erect, the texture thereof being hard and the leaves regularly spaced along the full length of the cane and the distinctive color pattern of its leaves with a narrow striping thereof represented by a single, narrow whitist marginal stripe, lengthwise through the center and margined with dark green on the upper surface and gray green on the bottom surface.

No references cited.

ROBERT E. BAGWILL, Primary Examiner